(12) United States Patent
Noguchi

(10) Patent No.: US 8,917,919 B2
(45) Date of Patent: Dec. 23, 2014

(54) ULTRASONIC OBSERVATION APPARATUS, OPERATION METHOD OF THE SAME, AND COMPUTER READABLE RECORDING MEDIUM

(71) Applicant: Olympus Medical Systems Corp., Tokyo (JP)

(72) Inventor: Hiromasa Noguchi, Mitaka (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/051,837

(22) Filed: Oct. 11, 2013

(65) Prior Publication Data

US 2014/0099008 A1   Apr. 10, 2014

Related U.S. Application Data

(63) Continuation of application No. PCT/JP2013/062848, filed on May 7, 2013.

(30) Foreign Application Priority Data

May 30, 2012   (JP) .................................. 2012-123362

(51) Int. Cl.
G06K 9/00 (2006.01)
G06T 7/00 (2006.01)
A61B 8/08 (2006.01)

(52) U.S. Cl.
CPC ............. *G06T 7/0012* (2013.01); *A61B 8/5207* (2013.01); *A61B 8/5269* (2013.01); *A61B 8/085* (2013.01)
USPC ............................ 382/128; 382/274; 600/437

(58) Field of Classification Search
USPC ................................... 382/128, 274; 600/437
See application file for complete search history.

(56) References Cited

U.S. PATENT DOCUMENTS 6,508,768 B1 *   1/2003   Hall et al. ...................... 600/443
6,743,174 B2 *   6/2004   Ng et al. ........................ 600/437

(Continued)

FOREIGN PATENT DOCUMENTS

JP   2005-253827 A   9/2005
JP   2005-536289 A   12/2005

(Continued)

OTHER PUBLICATIONS

Alam et al., "Computer-aided diagnosis of breast lesions using a multifeature analysis procedure", 2002, Medical Imaging 2002: Ultrasonic Imaging and Signal Processing, 296-303.*

(Continued)

*Primary Examiner* — Jason Repko
*Assistant Examiner* — Katrina Fujita
(74) *Attorney, Agent, or Firm* — Scully, Scott, Murphy & Presser, P.C.

(57) ABSTRACT

An ultrasonic observation apparatus includes: a frequency analysis unit that calculates a frequency spectrum for each of a plurality of locations in a predetermined region of a subject by analyzing frequency of the ultrasonic wave at the plurality of locations; a frequency spectrum approximate equation calculation unit that calculates an approximate equation of the frequency spectrum at the each location calculated by the frequency analysis unit; a deviation calculation unit that calculates deviation between the frequency spectrum at the each location calculated by the frequency analysis unit and the approximate equation of the frequency spectrum calculated correspondingly with the frequency spectrum by the frequency spectrum approximate equation calculation unit; and a deviation display image data generation unit that generates information related to the deviation.

10 Claims, 10 Drawing Sheets

(56) References Cited

U.S. PATENT DOCUMENTS

| | | | |
|---|---|---|---|
| 7,892,188 B2* | 2/2011 | Walker et al. | 600/587 |
| 7,949,173 B2* | 5/2011 | Zhou et al. | 382/131 |
| 8,447,091 B2* | 5/2013 | Eda | 382/131 |
| 8,619,142 B2* | 12/2013 | Miyaki | 348/163 |
| 2004/0037455 A1 | 2/2004 | Klingensmith et al. | |
| 2004/0039286 A1 | 2/2004 | Kuban et al. | |
| 2004/0122326 A1 | 6/2004 | Nair et al. | |
| 2004/0152983 A1 | 8/2004 | Vince et al. | |
| 2005/0203405 A1 | 9/2005 | Tsujita | |
| 2006/0241486 A1 | 10/2006 | Nair et al. | |
| 2006/0241487 A1 | 10/2006 | Nair et al. | |
| 2006/0253033 A1 | 11/2006 | Nair et al. | |
| 2008/0051659 A1 | 2/2008 | Waki et al. | |
| 2008/0287795 A1 | 11/2008 | Klingensmith et al. | |
| 2011/0208017 A1 | 8/2011 | Kuban et al. | |
| 2011/0235892 A1 | 9/2011 | Klingensmith et al. | |
| 2012/0310087 A1* | 12/2012 | Miyaki et al. | 600/440 |
| 2013/0012818 A1* | 1/2013 | Miyaki | 600/442 |
| 2013/0028497 A1 | 1/2013 | Klingensmith et al. | |
| 2013/0030296 A1* | 1/2013 | Miyaki | 600/442 |
| 2013/0035594 A1* | 2/2013 | Eda | 600/442 |

FOREIGN PATENT DOCUMENTS

| | | | | |
|---|---|---|---|---|
| JP | 2007-524431 A | | 8/2007 | |
| JP | 2010-193944 A | | 9/2010 | |
| JP | WO2012063928 | * | 5/2012 | A61B 8/00 |
| JP | WO2012063929 | * | 5/2012 | A61B 8/00 |
| JP | WO2012063975 | * | 5/2012 | A61B 8/08 |
| JP | WO2012063976 | * | 5/2012 | A61B 8/08 |
| JP | WO2012063977 | * | 5/2012 | A61B 8/00 |
| WO | WO 2004/017835 A1 | | 3/2004 | |
| WO | WO 2004/069027 A2 | | 8/2004 | |
| WO | WO 2005/122906 A1 | | 12/2005 | |

OTHER PUBLICATIONS

English translation of International Search Report from related International Application No. PCT/JP2013/062848, dated Jun. 11, 2013.

* cited by examiner

ULTRASONIC OBSERVATION APPARATUS, OPERATION METHOD OF THE SAME, AND COMPUTER READABLE RECORDING MEDIUM

CROSS-REFERENCE TO RELATED APPLICATIONS

This application is a continuation of PCT International Application No. PCT/JP2013/062848, filed on May 7, 2013 and claiming the benefit of priority from Japanese Patent Application No. 2012-123362, filed on May 30, 2012, and the entire contents of the Japanese patent application and the PCT international application are incorporated herein by reference.

BACKGROUND OF THE INVENTION

1. Field of the Invention

The present invention relates to an ultrasonic observation apparatus for observing tissue of a subject using ultrasonic waves, a method of operating the ultrasonic observation apparatus, and a computer readable recording medium.

2. Description of the Related Art

As a technique of examining breast cancer or the like using ultrasonic waves, a technique called ultrasonic elastography has been known (for example, see International Publication WO 2005/122906). The ultrasonic elastography is a technique utilizing the fact that hardness of cancer or tumor tissue in a living organism differs depending on progress of the disease or on the living organism. In this technique, with the location to be examined being compressed from the outside, an amount of strain or a modulus of elasticity of body tissue at the examined location is measured using ultrasonic waves and results of this measurement are image-displayed as a tomographic image.

SUMMARY OF THE INVENTION

An ultrasonic observation apparatus according to the present invention is an ultrasonic observation apparatus that transmits an ultrasonic wave to a subject, receives the ultrasonic wave reflected by the subject, and performs image display based on the received ultrasonic wave, and the ultrasonic observation apparatus includes: a frequency analysis unit that calculates a frequency spectrum for each of a plurality of locations in a predetermined region of the subject by analyzing frequency of the ultrasonic wave at the plurality of locations; a frequency spectrum approximate equation calculation unit that calculates an approximate equation of the frequency spectrum at the each location calculated by the frequency analysis unit; a deviation calculation unit that calculates deviation between the frequency spectrum at the each location calculated by the frequency analysis unit and the approximate equation of the frequency spectrum calculated correspondingly with the frequency spectrum by the frequency spectrum approximate equation calculation unit; and a deviation display image data generation unit that generates information related to the deviation calculated by the deviation calculation unit.

A method of operating an ultrasonic observation apparatus according to the present invention is a method of operating an ultrasonic observation apparatus that transmits an ultrasonic wave to a subject, receives the ultrasonic wave reflected by the subject, and performs image display based on the received ultrasonic wave, and the method includes: calculating, by a frequency analysis unit, a frequency spectrum for each of a plurality of locations in a predetermined region of the subject by analyzing frequency of the ultrasonic wave at the plurality of locations; calculating, by a frequency spectrum approximate equation calculation unit, an approximate equation of the frequency spectrum at the each location, by approximating the frequency spectrum of the each location; calculating, by a deviation calculation unit, deviation between the frequency spectrum at the each location and the approximate equation of the frequency spectrum calculated correspondingly with the frequency spectrum; and generating, by a deviation display image data generation unit, information related to the deviation.

A non-transitory computer readable recording medium storing an executable program according to the present invention is a non-transitory computer readable recording medium storing an executable program that instructs a processer to execute: calculating, by a frequency analysis unit, a frequency spectrum for each of a plurality of locations in a predetermined region of a subject by analyzing frequency of an ultrasonic wave at the plurality of locations; calculating, by a frequency spectrum approximate equation calculation unit, an approximate equation of the frequency spectrum at the each location, by approximating the frequency spectrum of the each location; calculating, by a deviation calculation unit, deviation between the frequency spectrum at the each location and the approximate equation of the frequency spectrum calculated correspondingly with the frequency spectrum; and generating, by a deviation display image data generation unit, information related to the deviation.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

An embodiment for carrying out the present invention (hereinafter referred to as "embodiment") is hereinafter described with reference to the attached drawings.

Figure 1:
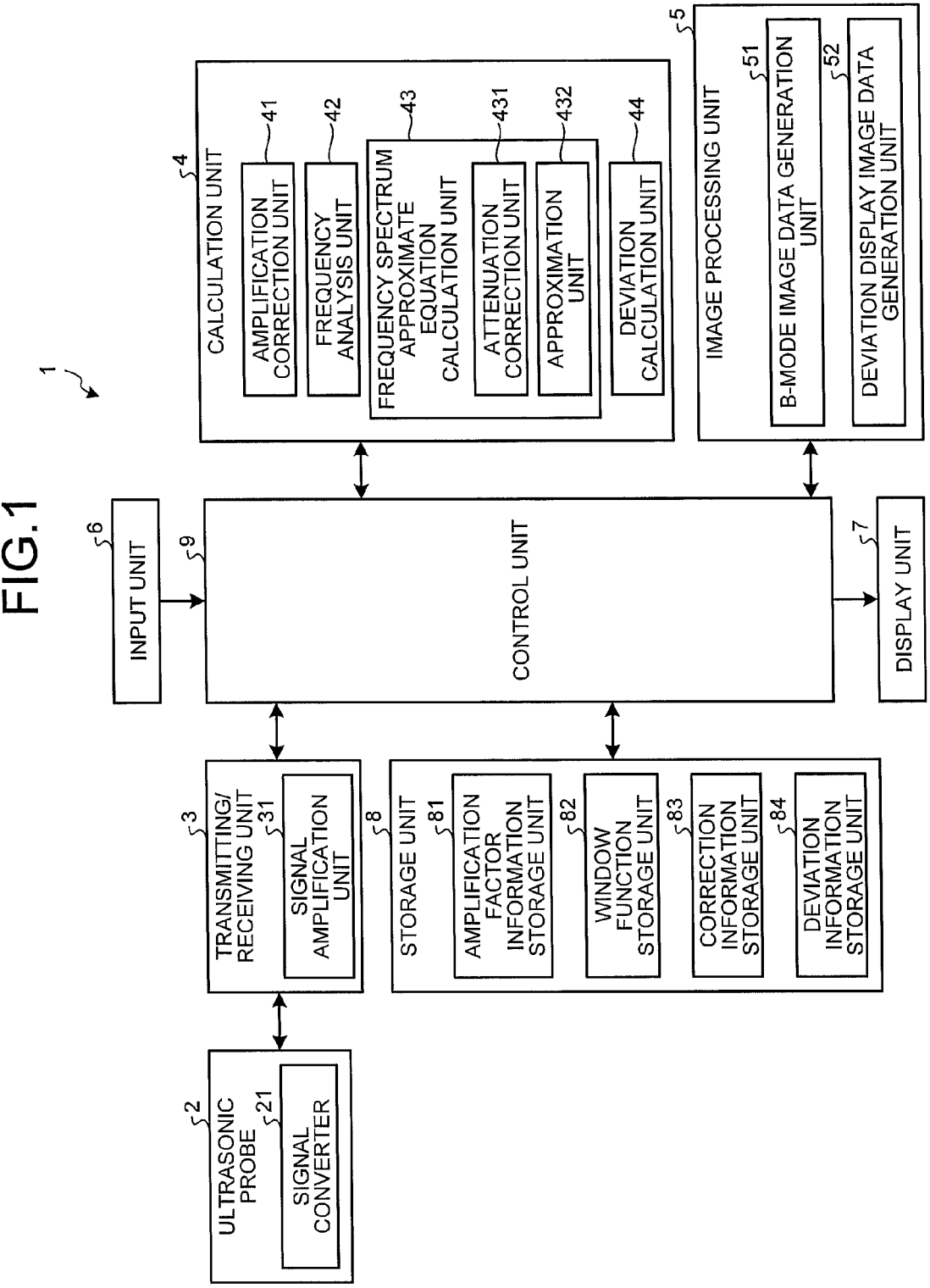
FIG. 1 is a block diagram depicting a structure of an ultrasonic observation apparatus according to an embodiment of the present invention.

FIG. 1 is a block diagram depicting a structure of an ultrasonic observation apparatus according to an embodiment of the present invention. An ultrasonic observation apparatus 1 depicted in this figure is an apparatus for observing a subject to be diagnosed using ultrasonic waves.

The ultrasonic observation apparatus 1 includes: an ultrasonic probe 2 that outputs ultrasonic pulses to the outside and receives ultrasonic echoes reflected outside; a transmitting/receiving unit 3 that transmits and receives electric signals to and from the ultrasonic probe 2; a calculation unit 4 that performs predetermined calculation on an electric echo signal obtained by converting the ultrasonic echo; an image processing unit 5 that generates image data corresponding to the electric echo signal obtained by converting the ultrasonic echoes; an input unit 6 that is realized using an interface such as a keyboard, a mouse, or a touch panel and receives input of various information; a display unit 7 that is realized using a display panel such as a liquid crystal panel or an organic EL panel and displays various information including the image generated by the image processing unit 5; a storage unit 8 that stores various information for observing the subject using the ultrasonic waves; and a control unit 9 controlling the operation of the ultrasonic observation apparatus 1.

The ultrasonic probe 2 includes a signal converter 21 that converts the electric pulse signal received from the transmitting/receiving unit 3 into an ultrasonic pulse (acoustic pulse signal) and converts the ultrasonic echo reflected on the outside subject into the electric echo signal. The ultrasonic probe 2 may either mechanically scan an ultrasonic vibrator or electronically scan a plurality of ultrasonic vibrators.

The transmitting/receiving unit 3 is electrically connected to the ultrasonic probe 2, transmits the pulse signal to the ultrasonic probe 2, and receives the echo signal from the ultrasonic probe 2. Specifically, the transmitting/receiving unit 3 generates the pulse signal on the basis of predetermined waveform and transmitting timing, and transmits the generated pulse signal to the ultrasonic probe 2.

Figure 2:
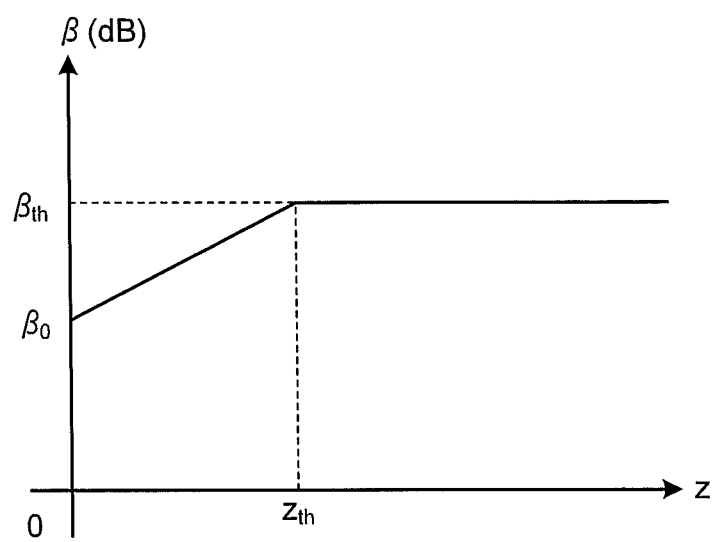
FIG. 2 is a diagram depicting a relation between amplification factor and received depth in an amplification process performed by a signal amplification unit of an ultrasonic observation apparatus according to an embodiment of the present invention.

The transmitting/receiving unit 3 includes a signal amplification unit 31 that amplifies the echo signal. Specifically, the signal amplification unit 31 performs STC (sensitivity time control) correction for amplifying the echo signal so that the echo signal with larger received depth is amplified at a higher amplification factor. FIG. 2 is a diagram depicting the relation between the amplification factor and the received depth of the echo signal. The received depth z illustrated in FIG. 2 corresponds to the quantity calculated based on the passage time from the time when the reception of the ultrasonic wave is started. As illustrated in FIG. 2, the amplification factor $\beta$ (dB) linearly increases from $\beta_0$ to $\beta_{th}$ along with the increase in received depth "z" if the received depth "z" is less than the threshold value $z_{th}$. If the received depth "z" is greater than or equal to the threshold value $z_{th}$, the amplification factor $\beta$ is of a certain value $\beta_{th}$. The threshold value $z_{th}$ is of a value at which the ultrasonic signal received from the subject is mostly attenuated and the noise becomes dominant. More generally, if the received depth z is less than the threshold value $z_{th}$, the amplification factor $\beta$ may be monotonically increased along with the increase in received depth z.

The transmitting/receiving unit 3 performs the process such as filtering on the echo signal amplified by the signal amplification unit 31, and thereafter performs the A/D conversion thereon to generate and output a digital RF signal. If the ultrasonic probe 2 electronically scans the plural ultrasonic vibrators, the transmitting/receiving unit 3 includes a multichannel circuit for beam synthesis in accordance with the plural ultrasonic vibrators.

The calculation unit 4 includes: an amplification correction unit 41 that performs the amplification correction for making the amplification factor constant regardless of the received depth, with respect to the digital RF signal output from the transmitting/receiving unit 3; a frequency analysis unit 42 that calculates the frequency spectrum by performing frequency analysis by subjecting the amplification-corrected digital RF signal to fast Fourier transformation (FFT); a frequency spectrum approximate equation calculation unit 43 that calculates an approximate equation of the frequency spectrum at each position calculated by the frequency analysis unit 42; and a deviation calculation unit 44 that calculates deviation between the frequency spectrum at each position calculated by the frequency analysis unit 42 and the approximate equation of the frequency spectrum calculated, correspondingly with the frequency spectrum, by the frequency spectrum approximate equation calculation unit 43.

Figure 3:
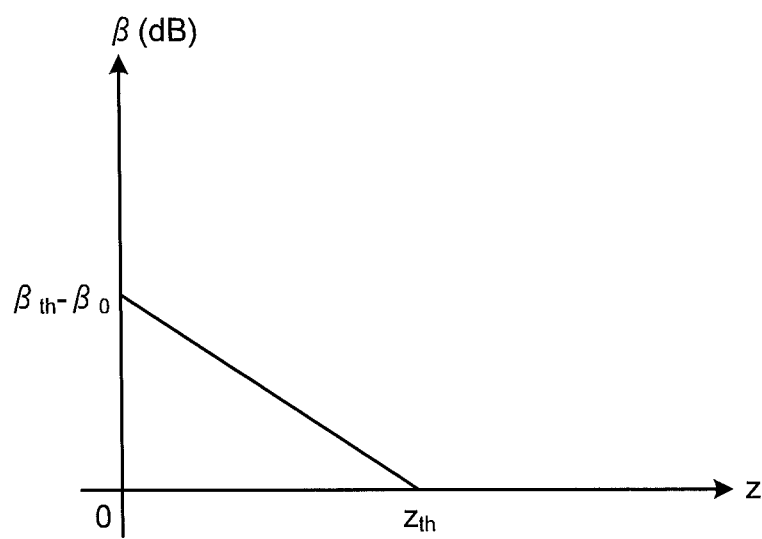
FIG. 3 is a diagram depicting a relation between amplification factor and received depth in an amplification process performed by an amplification correction unit of an ultrasonic observation apparatus according to an embodiment of the present invention.

FIG. 3 is a diagram depicting a relation between the amplification factor and the received depth in the amplification process performed by the amplification correction unit 41. As depicted in FIG. 3, when the received depth z is zero, the amplification factor $\beta$ (dB) in the amplification process performed by the amplification correction unit 41 is of the maximum value "$\beta_{th}-\beta_0$"; when the received depth z reaches the threshold value $z_{th}$ from zero, the amplification factor $\beta$ linearly decreases; and when the received depth z is greater than or equal to the threshold value $z_{th}$, the amplification factor $\beta$ is zero. By subjecting the digital RF signal to amplification-correction in the amplification correction unit 41 by the amplification factor defined as above, it is possible to offset the influence of the STC correction in the signal amplification unit 31 and output the signal at the constant amplification factor $\beta_{th}$. Needless to say, the relation between the amplification factor $\beta$ and the received depth z of the amplification correction unit 41 becomes different depending on the relation between the amplification factor and the received depth in the signal amplification unit 31.

The frequency analysis unit 42 calculates, with respect to each sound ray (line data), the frequency spectrum at a plurality of positions (data positions) on the sound ray by performing fast Fourier transformation on an FFT data group including predetermined data volume. The frequency spectrum exhibits different tendency depending on tissue characterization of the subject. This is because the frequency spectrum has correlation with the size, density, acoustic impedance, or the like of the subject as a scattering body that scatters the ultrasonic waves. In this embodiment, "tissue characterization" refers to any of cancer, endocrine tumor, mucinous tumor, normal tissue, blood vessel, and the like.

Figure 4:
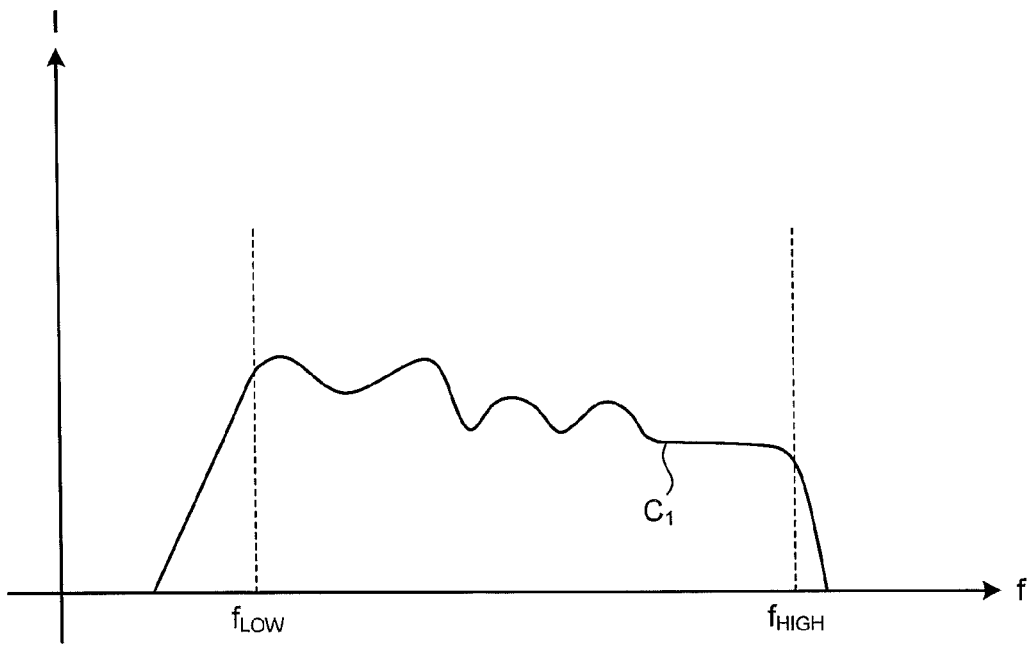
FIG. 4 is a diagram depicting an example of a frequency spectrum calculated by a frequency analysis unit of an ultrasonic observation apparatus according to an embodiment of the present invention.

FIG. 4 is a diagram depicting an example of the frequency spectrum calculated by the frequency analysis unit 42. In FIG. 4, the horizontal axis f represents the frequency while the vertical axis I represents the intensity. In the frequency spectrum curve $C_1$ in FIG. 4, the lower-limit frequency $f_{LOW}$ and the upper-limit frequency $f_{HIGH}$ of the frequency spectrum correspond to the parameters determined based on the frequency band of the ultrasonic probe 2, the frequency band of the pulse signal transmitted from the transmitting/receiving unit 3, and the like, and for example, $f_{LOW}=3$ MHz and $f_{HIGH}=10$ MHz. In this embodiment, the curved line and the straight line are formed of a group of discrete points.

The frequency spectrum approximate equation calculation unit 43 includes: an attenuation correction unit 431 that performs, with respect to the frequency spectrum calculated by the frequency analysis unit 42, an attenuation correction process for reducing the contribution of the attenuation of the ultrasonic waves depending on the frequency and the received depth of the ultrasonic wave; and an approximation unit 432 that calculates, by regression analysis, the approximate equation of the frequency spectrum attenuation-corrected by the attenuation correction unit 431.

In general, the attenuation amount "A" of the ultrasonic waves is defined as follows.

$$A = 2\alpha z f \quad (1)$$

Herein, α represents the attenuation ratio, "z" represents the received depth of the ultrasonic waves, and "f" represents the frequency. As is clear from Equation (1), the attenuation amount "A" is in proportion to the frequency "f". The specific value of the attenuation ratio α is, for a living organism, 0.0 to 1.0 (dB/cm/MHz), and preferably 0.3 to 0.7 (dB/cm/MHz), and is determined depending on the kind of the observation target. For example, if the observation target is pancreas, α=0.6 (dB/cm/MHz). In this embodiment, the value of the attenuation ratio α may be changed by the input from the input unit 6.

Figure 5:
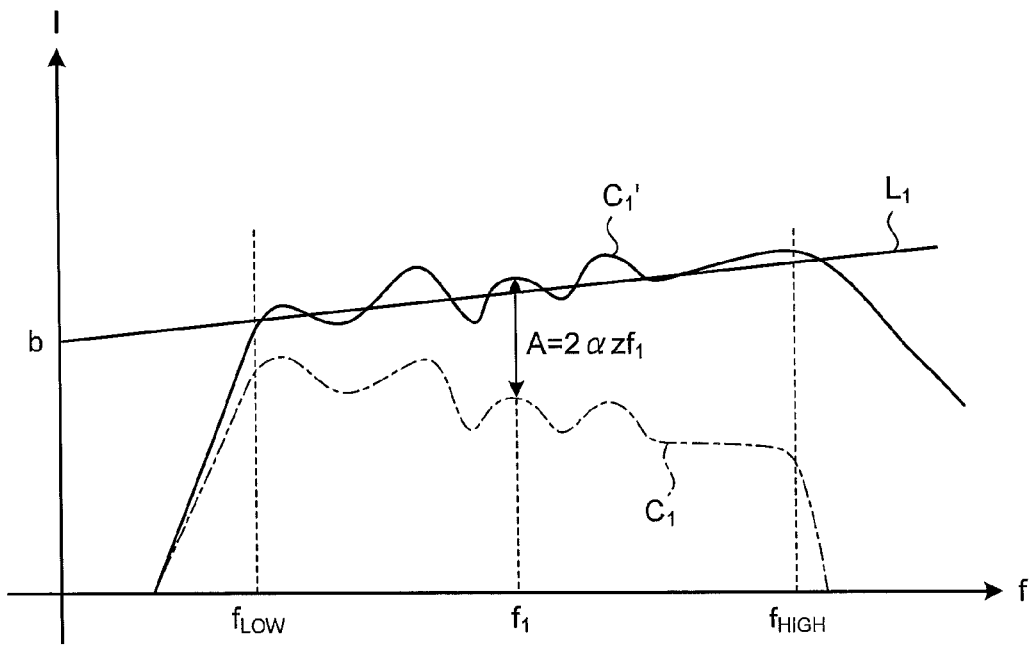
FIG. 5 is a schematic diagram depicting an outline of an attenuation correction process performed by an ultrasonic observation apparatus according to an embodiment of the present invention.

FIG. 5 is a schematic diagram depicting an outline of an attenuation correction process performed by the attenuation correction unit 431. As depicted in FIG. 5, the attenuation correction unit 431 performs, on the frequency spectrum curve $C_1$, correction of adding the attenuation amount "A" of Equation (1) to the intensity "I" at all the frequencies "f" ($f_{LOW} \leq f \leq f_{HIGH}$) in the band. Thus, a new frequency spectrum curve $C_1'$ with the contribution of the attenuation due to the propagation of the ultrasonic waves reduced is obtained. More specifically, by the attenuation correction process of the attenuation correction unit 431, it is possible to suppress the signal intensity from being reduced due to the influence of the attenuation in a region where the received depth is large and the image from becoming darker, and to obtain an image with uniform brightness over the entire screen.

The approximation unit 432 approximates the frequency spectrum attenuation-corrected by the attenuation correction unit 431 with a linear equation by regression analysis. Specifically, the approximation unit 432 calculates the slope "a" and the intercept "b" of the linear equation by regression analysis. "Spectrum intensity" herein described refers to any of parameters such as voltage, power, sound pressure, and acoustic energy. The straight line $L_1$ of FIG. 5 is a regression line corresponding to the linear equation that is the approximate equation of the frequency spectrum curve $C_1'$. The approximate equation calculated by the frequency spectrum approximate equation calculation unit 43 is not limited to a linear equation and may be a polynomial equation such as a quadratic equation. However, from the viewpoint of using the deviation from the frequency spectrum curve as the index of determining the tissue characterization, a linear equation is preferably employed as the approximate polynomial equation.

Figure 6:
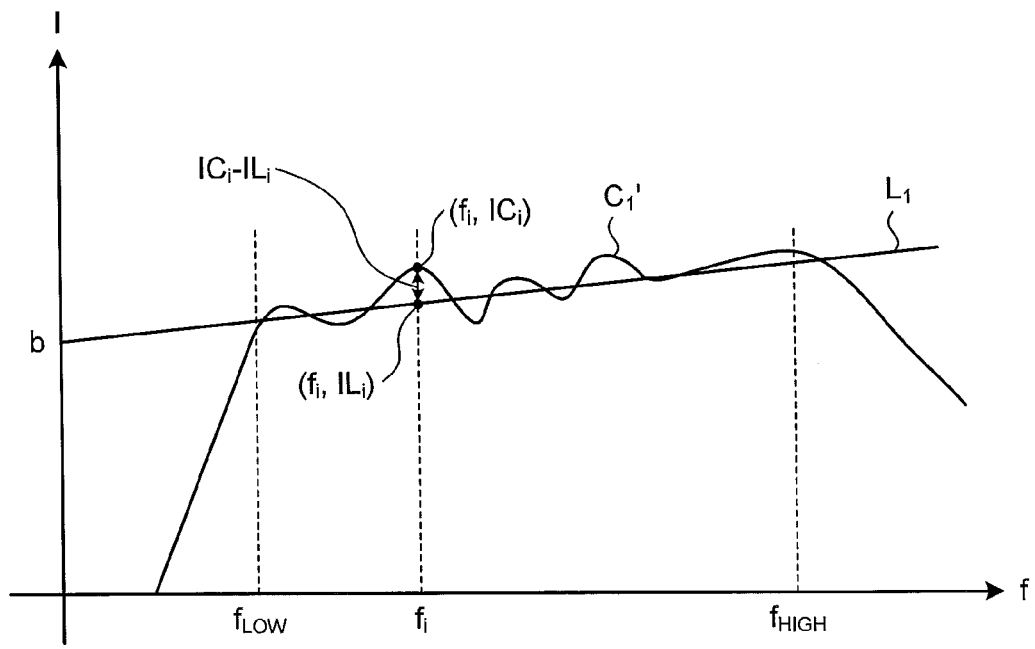
FIG. 6 is a schematic diagram depicting an outline of a deviation calculation process performed by an ultrasonic observation apparatus according to an embodiment of the present invention.

The deviation calculation unit 44 calculates the deviation between the frequency spectrum at each data position and the approximate equation of the frequency spectrum. Specifically, the deviation calculation unit 44 calculates as the deviation, the average of the sum of squares of the deviation on each point (corresponding to each data position on the sound ray) in the region of interest set in advance in the B-mode image as the predetermined region of the subject. FIG. 6 is a diagram for describing the sum of squares of the deviation. The sum of squares is defined as follows.

$$S = \sum_i (IC_i - IL_i)^2 \quad (2)$$

Herein, $IC_i$ on the right hand side of Equation (2) represents the intensity of the frequency spectrum curve $C_1'$ at the frequency $f_i$. Further, $IL_i$ on the right hand side of Equation (2) represents the intensity of the regression line $L_1$ at the frequency $f_i$. Further, the sum of the right hand side of the equation refers to the sum of all the "i"s satisfying $f_{LOW} \leq f \leq f_{HIGH}$.

The image processing unit 5 includes: a B-mode image data generation unit 51 that generates the B-mode image data from the echo signal; and a deviation display image data generation unit 52 that generates deviation display image data including the information related to the deviation calculated by the deviation calculation unit 44.

Figure 7:
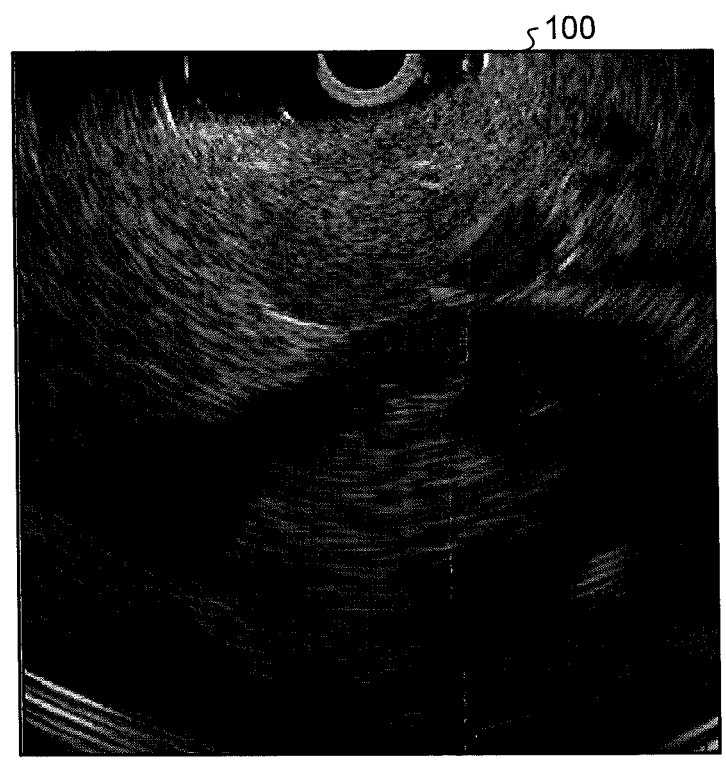
FIG. 7 is a diagram depicting a display example of a B-mode image in a display unit of an ultrasonic observation apparatus according to an embodiment of the present invention.

The B-mode image data generation unit 51 performs signal processing on a digital signal using a known technique, such as band-pass filter, logarithmic transformation, gain processing, or contrast processing, and, for example, decimates the data according to the data step width determined in accordance with the display range of the image in the display unit 7, thereby generating the B-mode image data. FIG. 7 is a diagram depicting the display example of the B-mode image in the display unit 7. A B-mode image 100 in this drawing is a grayscale image in which the values of R (red), G (green), and B (blue), which are variables when the RGB color system is employed as the color system, are matched among one another. The region of interest in the B-mode image may be set arbitrarily by a user through the input unit 6.

The input unit 6 is formed by an interface such as a keyboard, a mouse, or a touch panel. The input unit 6 accepts input of information for specifying the region of interest from a user of the ultrasonic observation apparatus 1 having seen the image generated by the image processing unit 5.

The storage unit 8 includes: an amplification factor information storage unit 81 that stores information on the amplification factor to which the signal amplification unit 31 and the amplification correction unit 41 refer when the amplification process is performed; a window function storage unit 82 that stores the window function used when the frequency analysis unit 42 performs the frequency analysis process; a correction information storage unit 83 that stores the correction information to which the attenuation correction unit 431 refers when performing a process; and a deviation information storage unit 84 that stores information related to the deviation including the calculation result by the deviation calculation unit 44.

The amplification factor information storage unit 81 stores the relations between the received depths and the amplification factors depicted in FIG. 2 and FIG. 3. The window function storage unit 82 stores at least one of window functions such as Hamming, Hanning, and Blackman. The correction information storage unit 83 stores the information related to the attenuation correction including Equation (1). The deviation information storage unit 84 stores the information related to the deviation including the calculation result by the deviation calculation unit 44.

The storage unit 8 is achieved by using a ROM in which an operation program of the ultrasonic observation apparatus 1, a program for activating a predetermined OS, and the like are stored, a RAM in which calculation parameters, data, and the like of each process are stored, for example.

The control unit 9 is achieved using a CPU having calculation and control functions. The control unit 9 executes various calculation processes related to the operation method of the ultrasonic observation apparatus 1 by reading out the information stored and held in the storage unit 8 and various programs including the operation program of the ultrasonic observation apparatus 1, thereby generally controlling the ultrasonic observation apparatus 1.

The operation program of the ultrasonic observation apparatus 1 may be widely distributed by recording the program in a computer readable recording medium such as a hard disk, flash memory, a CD-ROM, a DVD-ROM, or a flexible disk.

Figure 8:
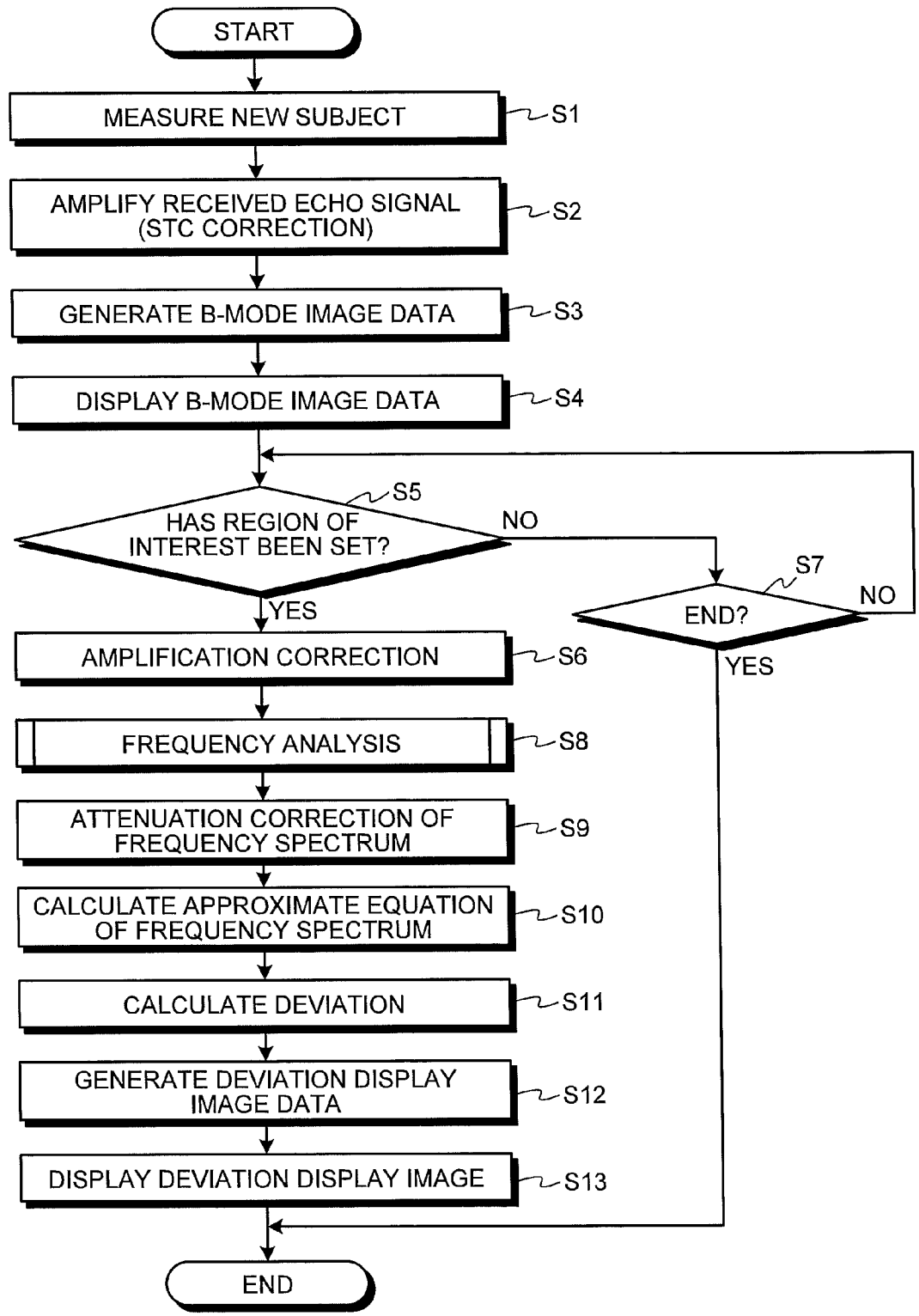
FIG. 8 is a flowchart depicting an outline of a process of an ultrasonic observation apparatus according to an embodiment of the present invention.

FIG. 8 is a flowchart depicting an outline of a process by the ultrasonic observation apparatus 1 having the above structure. In FIG. 8, the ultrasonic observation apparatus 1 performs measurement of a new subject with the ultrasonic probe 2 (Step S1).

Subsequently, upon reception of the echo signal from the ultrasonic probe 2, the signal amplification unit 31 amplifies the echo signal (Step S2). Here, the signal amplification unit 31 amplifies the signal based on the relation between the received depth and the amplification factor depicted in FIG. 2.

After that, the B-mode image data generation unit 51 generates the B-mode image data using the B-mode image echo signal output from the transmitting/receiving unit 3 (Step S3).

Subsequently, the control unit 9 performs control for causing the display unit 7 to display the B-mode image corresponding to the B-mode image data generated by the B-mode image data generation unit 51 (Step S4). An example of the B-mode image displayed by the display unit 7 is a B-mode image 100 depicted in FIG. 7.

After that, if a region of interest has been set via the input unit 6 (Step S5: Yes), the amplification correction unit 41 corrects the signal output from the transmitting/receiving unit 3 to make the amplification factor constant regardless of the received depth (Step S6). Here, the amplification correction unit 41 performs the amplification process on the basis of the relation between the received depth and the amplification factor depicted in FIG. 3. As the region of interest, a region corresponding to the entire B-mode image may be set.

If the region of interest has not been set (Step S5: No), the ultrasonic observation apparatus 1 ends the process upon input of the process end order through the input unit 6 (Step S7: Yes). In contrast, if the region of interest has not been set (Step S5: No) and the process end order is not input through the input unit 6 (Step S7: No), the ultrasonic observation apparatus 1 returns to Step S5.

After Step S6, the frequency analysis unit 42 calculates the frequency spectrum by performing frequency analysis by FFT calculation (Step S8). In this Step S8, the entire image region may be set as the region of interest.

Figure 9:
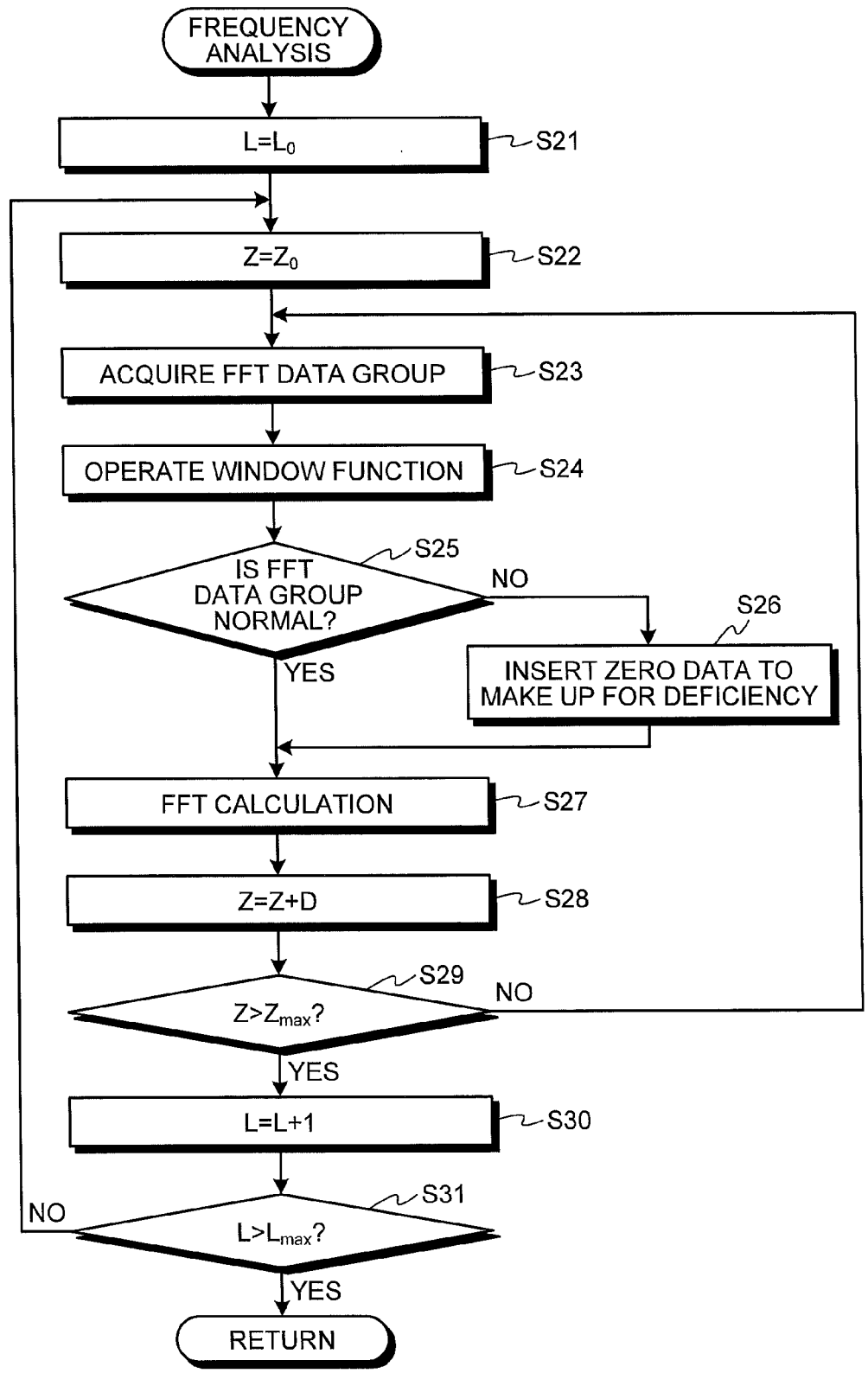
FIG. 9 is a flowchart depicting an outline of a process performed by a frequency analysis unit of an ultrasonic observation apparatus according to an embodiment of the present invention.

Here, a process by the frequency analysis unit 42 (Step S8) is described in detail with reference to the flowchart of FIG. 9. First, the frequency analysis unit 42 sets the sound ray number "L" of the sound ray as the first analysis target to an initial value $L_0$ (Step S21). The initial value $L_0$ may be given to a sound ray received by the transmitting/receiving unit 3 first or to a sound ray corresponding to one of right and left boundary positions of the region of interest set by the input unit 6.

Figure 10:
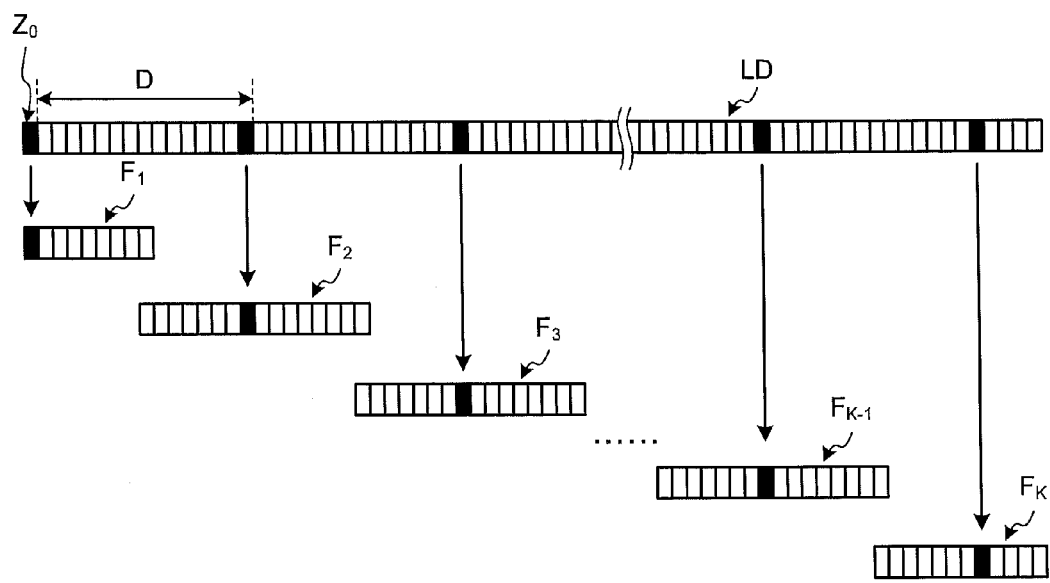
FIG. 10 is a schematic diagram of a data arrangement of one sound ray.

Subsequently, the frequency analysis unit 42 calculates the frequency spectrum at all the plural data positions set on one sound ray. First, the frequency analysis unit 42 sets the initial value $Z_0$ of the data position "Z" (corresponding to the received depth) representing a group of data (FFT data group) acquired for the FFT calculation (Step S22). FIG. 10 is a schematic diagram depicting a data arrangement of one sound ray. In a sound ray "LD" in the drawing, a white or black rectangle means one data. The sound ray LD is discretized at time intervals corresponding to a sampling frequency (for example, 50 MHz) in the A/D conversion performed by the transmitting/receiving unit 3. In FIG. 10, the first data of the sound ray LD is set as the initial value $Z_0$ of the data position "Z". FIG. 10 is just an example and the position of the initial value $Z_0$ may be set arbitrarily. For example, the data position "Z" corresponding to the upper end position of the region of interest may be set as the initial value $Z_0$.

After that, the frequency analysis unit 42 acquires the FFT data group of the data position "Z" (Step S23), and operates the window function stored in the window function storage unit 82 on the acquired FFT data group (Step S24). By operating the window function on the FFT data group in this manner, it is possible to prevent the FFT data group from becoming discontinuous at the boundary and the artifact from occurring.

Subsequently, the frequency analysis unit 42 determines whether the FFT data group at the data position "Z" is a normal data group (Step S25). Here, the FFT data group needs to have a data quantity of the power of 2. The data quantity of the FFT data group is hereinafter assumed to be $2^n$ ("n" is a positive integer). The FFT data group being normal means that the data position "Z" is the $2^{n-1}$-th position from the front in the FFT data group. In other words, the FFT data group being normal means that there are $2^{n-1}-1$ ($=N$) data before the data position "Z", and $2^{n-1}$ ($=M$) data exist behind the data position "Z". In FIG. 10, n=4 (N=7, M=8) and the FFT data groups $F_2$, $F_3$, and $F_{K-1}$ are normal but the FFT groups $F_1$ and $F_K$ are abnormal.

If the FFT data group of the data position Z is determined to be normal as a result of the determination of Step S25 (Step S25: Yes), the frequency analysis unit 42 proceeds to Step S27 described later.

If the FFT data group at the data position Z is determined to be abnormal as a result of the determination of Step S25 (Step S25: No), the frequency analysis unit 42 generates the normal FFT data group by inserting zero data to make up for deficiency (Step S26). The FFT data group determined to be abnormal in Step S25 is operated by the window function before the addition of the zero data. Therefore, the data do not become discontinuous even if the zero data are inserted into the FFT data group. After Step S26, the frequency analysis unit 42 transits to Step S27 as described later.

In Step S27, the frequency analysis unit 42 performs the FFT calculation using the FFT data group, thereby providing the frequency spectrum (Step S27). An example of such a frequency spectrum is the frequency spectrum curve $C_1$ depicted in FIG. 4.

Subsequently, the frequency analysis unit 42 calculates the data position "Z" of the FFT data group as the next analysis target by adding a predetermined data step width "D" to the data position "Z" (Step S28). The data step width "D" is preferably the same as the data step width used when the B-mode image data generation unit 51 generates the B-mode image data, but if the amount of calculation in the frequency analysis unit 42 is desired to be reduced, the data step width "D" may be larger than the data step width used by the B-mode image data generation unit 51. In FIG. 10, D=15.

After that, the frequency analysis unit 42 determines whether the data position "Z" is greater than the final data position $Z_{max}$ (Step S29). The final data position $Z_{max}$ may be the data length of the sound ray LD or the data position corresponding to the lower end of the region of interest. If the data position "Z" is greater than the final data position $Z_{max}$ as a result of the determination (Step S29: Yes), the frequency analysis unit 42 increases the sound ray number "L" by one (Step S30). Meanwhile, if the data position "Z" is less than or equal to the final data position $Z_{max}$ (Step S29: No), the frequency analysis unit 42 returns to Step S23. In this manner, the frequency analysis unit 42 performs the FFT calculation on FFT data groups as many as $[\{(Z_{max}-Z_0)/D\}+1]$ (=K) with respect to one sound ray LD. Here, [X] represents the largest integer not greater than "Z".

If the sound ray number "L" after the addition in Step S30 is greater than the final sound ray number $L_{max}$ (Step S31: Yes), the frequency analysis unit 42 returns to the main routine depicted in FIG. 8. Meanwhile, if the sound ray number "L" after the addition in Step S30 is less than or equal to the final sound ray number L. (Step S31: No), the frequency analysis unit 42 returns to Step S22.

Thus, the frequency analysis unit 42 performs the FFT calculation K times with respect to each of the $(L_{max}-L_0+1)$ sound rays. The final sound ray number $L_{max}$ may, for example, be given to the final sound ray received by the transmitting/receiving unit 3 or to the sound ray corresponding to any one of left and right boundaries of the region of interest. The total number $(L_{max}-L_0+1) \times K$ of the FFT calculations performed by the frequency analysis unit 42 on all the sound rays is set as "P".

Subsequent to the frequency analysis process of Step S8 as described above, the attenuation correction unit 431 performs the attenuation correction on the frequency spectrum calculated by the frequency analysis unit 42 through the FFT calculation (Step S9). The attenuation correction unit 431 calculates the attenuation amount "A" of the ultrasonic waves by obtaining the data position "Z" on the basis of the sampling frequency of the data and substituting the data position "Z" for the received depth "z" of the above Equation (1). After that, the attenuation correction unit 431 performs the attenuation correction of the frequency spectrum using the attenuation amount "A" calculated for each frequency. An example of the result of the attenuation correction by the attenuation correction unit 431 is the spectrum curve $C_1'$ depicted in FIG. 6.

Here, the specific example of the calculation for obtaining the data position "Z" by the attenuation correction unit 431 is described. If the sampling frequency of the data is 50 MHz, the time interval of the sampling is 1/50 (MHz)=20 (nsec). Here, if the ultrasonic speed is 1530 (m/sec), the sampling distance interval of the data is 1530 (m/sec)×20 (nsec)/2=0.0153 (mm). Assuming that the data step width "D" from the first data of the sound ray LD to the data position of the FFT data group to be processed is "k", the data position "Z" is 0.0153 k (mm).

Subsequently, the approximation unit 432 performs the regression analysis on the frequency spectrum obtained in Step S9, thereby calculating the approximate equation of the frequency spectrum (Step S10). Specifically, the approximation unit 432 calculates the linear expression for approximating the frequency spectrum of the frequency band $(f_{LOW} < f < f_{HIGH})$ through regression analysis, thereby extracting the slope "a" and the intercept "b" featuring this linear expression. A specific example of the regression line corresponding to the approximate equation calculated as described is the line $L_1$ depicted in FIG. 6.

After that, the deviation calculation unit 44 calculates the deviation (Step S11). Specifically, the deviation calculation unit 44 calculates the sum of squares of the deviation (see Equation (2)) at each point in the region of interest and then calculates the average thereof as the deviation.

Subsequently, the deviation display image data generation unit 52 generates the deviation display image data using the B-mode image data generated by the B-mode image data generation unit 51 and the deviation calculated by the deviation calculation unit 44 (Step S12).

Figure 11:
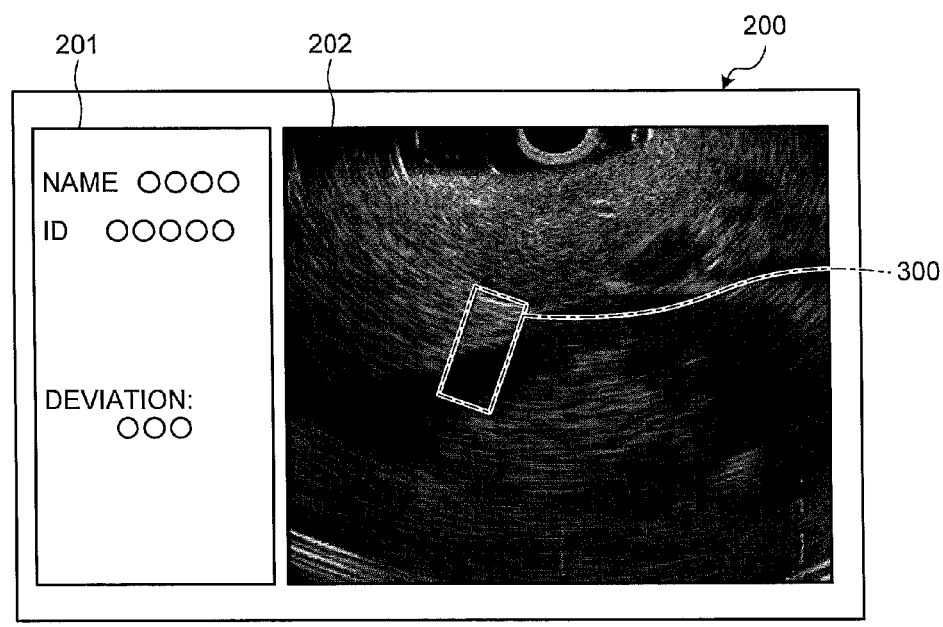
FIG. 11 is a diagram depicting a display example of a deviation display image displayed by a display unit of an ultrasonic observation apparatus according to an embodiment of the present invention.

After that, the display unit 7 displays the deviation display image generated by the deviation display image data generation unit 52 (Step S13). FIG. 11 is a diagram depicting the display example of the deviation display image displayed by the display unit 7. A deviation display image 200 depicted in the figure includes an information display unit 201 that displays the information including the identification information of a subject (name, ID number, etc.) and the deviation, and an image display unit 202 that displays a region 300 of interest of the deviation calculation target in the B-mode image 100 depicted in FIG. 7. A diagnostician having observed this deviation display image 200 is able to determine the tissue characterization of the region 300 of interest based on the B-mode image 100 and the value of the deviation. The information display unit 201 may further display information on the approximate equation or image information such as gain or contrast.

Lastly, the ultrasonic observation apparatus 1 finishes the series of processes. The ultrasonic observation apparatus 1 may repeat the processes of Steps S1 to S11 periodically.

Figure 12A:
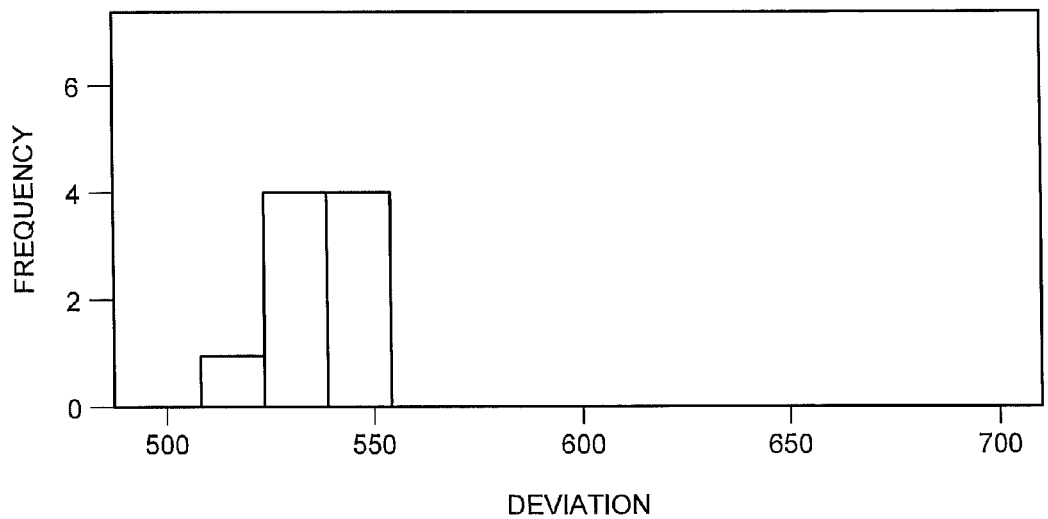
FIG. 12A is a histogram of a deviation distribution when tissue characterization in a pancreas is chronic pancreatitis.
Figure 12B:
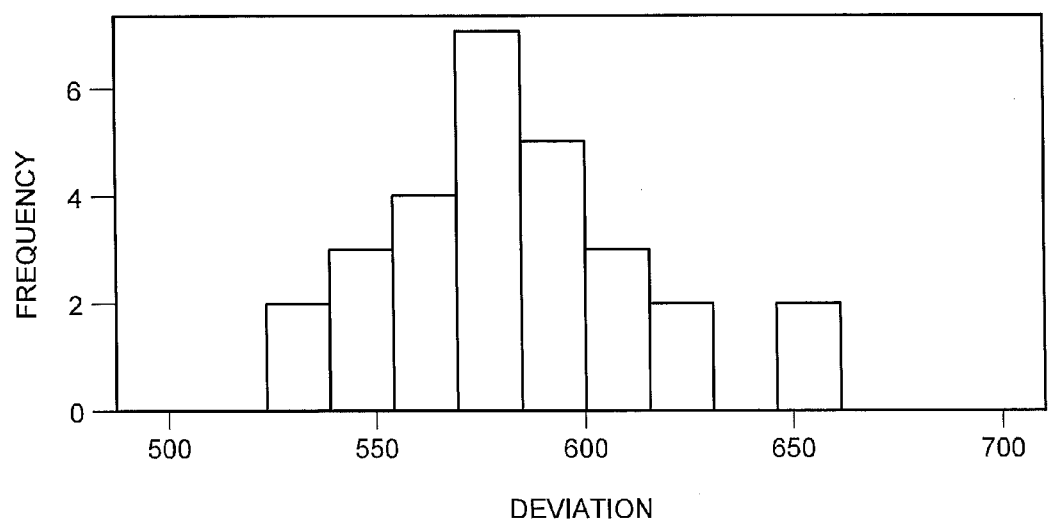
FIG. 12B is a histogram of a deviation distribution when tissue characterization of a pancreas is pancreatic cancer.

Next, with reference to FIG. 12A and FIG. 12B, description is made of an advantage of using the deviation as the index with which a diagnostician clearly recognize and accurately evaluate tissue characterization of a subject. FIG. 12A and FIG. 12B are histograms of distributions of deviation for each tissue characterization in pancreas. Specifically, FIG. 12A is a histogram of chronic pancreatitis and FIG. 12B is a histogram of pancreatic cancer. The comparison between the two histograms indicates that when the deviation is 550 or less, the tissue characterization is highly likely to be chronic pancreatitis, and when deviation is greater than 550, the tissue characterization is highly likely to be pancreatic cancer.

A reason for the significant difference in deviation between the chronic pancreatitis and the pancreatic cancer is considered. It is considered that chronic pancreatitis produces fibrae in normal pancreatic cells and thus the tissue is not uniform and the echo signal includes various frequency bands. In contrast to this, in pancreatic cancer, the cancer cells invade the surrounding tissue and thus uniform tissue of only the cancer cells is spread. Therefore, if the cancer cells reflect (or absorb) the ultrasonic waves with a particular frequency, the intensity becomes higher (or lower) in the narrow band in the frequency spectrum. Therefore, the frequency spectrum has high non-linearity and high deviation from the regression line. Thus, it is considered that the distributions of the deviation are clearly different because of the difference in non-linearity of the frequency spectra between the chronic pancreatitis and the pancreatic cancer.

In this embodiment, the results of calculating the deviation are displayed together with the B-mode image on the display unit 7 and thus a medical examiner such as a doctor is able to determine the tissue characterization of the subject together with the information from the B-mode image and more accurate diagnosis becomes possible.

In one embodiment of the present invention as described above, the deviation between the frequency spectrum of the ultrasonic wave at the plural positions within a predetermined region of the subject and the approximate equation of the frequency spectrum is calculated, and the deviation display image data including the information related to the deviation are generated. The deviation is closely related to the tissue characterization as aforementioned (see FIG. 12A and FIG. 12B). Therefore, according to this embodiment, it is possible to provide an index that allows a diagnostician to clearly recognize and accurately evaluate the tissue characterization of a subject.

Moreover, according to this embodiment, it is possible to provide a new method of evaluating tissue characterization by evaluating how far the frequency spectrum of the ultrasonic wave deviates from the regression line (linear expression) that is the approximate equation, i.e., the degree of non-linearity of the frequency spectrum. As a result, it is possible to realize a more accurate diagnosis method that can contribute to improvement in diagnosis accuracy of qualitative image diagnosis and to biopsy guides.

Further, according to this embodiment, because while the B-mode image data are generated based on the signal subjected to the STC correction of amplifying at the amplification factor according to the received depth, the frequency spectrum is calculated after offsetting the influence of the STC correction and performing the amplification correction for making the amplification factor constant regardless of the received depth, and after this frequency spectrum is subjected to the attenuation correction, the approximate equation of the frequency spectrum is calculated; it is possible to correctly eliminate the influence of the attenuation caused by the propagation of the ultrasonic waves and to prevent the reduction in the frame rate of the image data generated based on the received ultrasonic waves.

Figure 13:
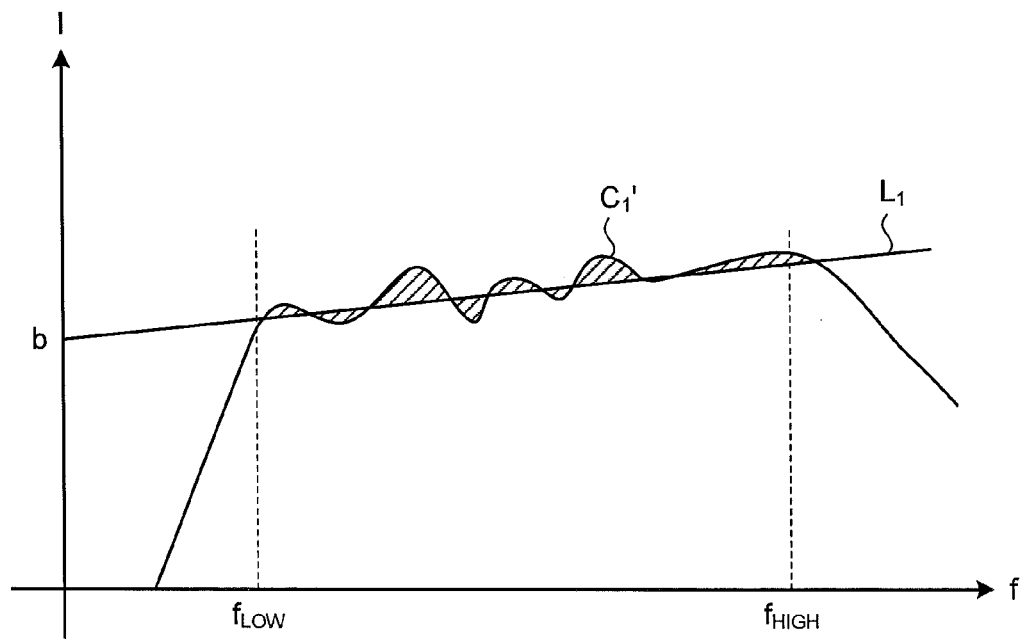
FIG. 13 is a schematic diagram depicting an outline of a process of calculating deviation performed by an ultrasonic observation apparatus according to an embodiment of the present invention.

The description has been made of the embodiments for carrying out the invention; however, the present invention is not limited to the above embodiments only. For example, in the present invention, the deviation calculation unit 44 may calculate the deviation using a quantity other than the sum of squares of the deviation. FIG. 13 is a diagram for describing another example of the deviation calculated by the deviation calculation unit 44. In this case, the deviation calculation unit 44 calculates, at each point in the region of interest, the area (deviation area) between the regression line $L_1$ and the frequency spectrum curve $C_1'$ within a predetermined range instead of the sum of square of the deviation, and calculates the average deviation area within the region of interest as the deviation. Application of the deviation thus calculated functions as an index that is effective in determining the tissue characterization like the above.

In the present invention, the deviation calculation unit 44 may calculate the sum of absolute values of differences between the intensity of the regression line $L_1$ and the intensity of the frequency spectrum curve $C_1'$ of the frequency in the band instead of the sum of squares S of the deviation.

$$S' = \sum_i |IC_i - IL_i| \quad (3)$$

Further, in the present invention, the deviation display image data generation unit 52 may generate the deviation display image data in which each point in the region of interest in the B-mode image has visual information corresponding to the deviation. As the visual information in this case, luminance, hue, chroma, brightness, or variables of a color space constituting a predetermined color system such as R (red), G (green), and (B) blue, may be used.

In the present invention, the amplification correction process by the amplification correction unit 41 and the attenuation correction process by the attenuation correction unit 431 may be performed collectively by the control unit 9. This process is equivalent to changing the definition of the attenuation amount of the attenuation correction process in Step S9 in FIG. 8 to Equation (4) without performing the amplification correction process in Step S6 in FIG. 8.

$$A' = 2\alpha z f + \gamma(z) \quad (4)$$

Herein, $\gamma(z)$ on the right hand side represents the difference between the amplification factors $\beta$ and $\beta_0$ at the received depth z, and is expressed as follows.

$$\gamma(z) = -\{(\beta_{th} - \beta_0)/z_{th}\}z + \beta_{th} - \beta_0 \ (z \leq z_{th}) \quad (5)$$

$$\gamma(z) = 0 \ (z > z_{th}) \quad (6).$$

Thus, the invention encompasses various embodiments without departing from technical ideas recited in the claims.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic observation apparatus that transmits an ultrasonic wave to a subject, receives the ultrasonic wave reflected by the subject, and performs image display based on the received ultrasonic wave, the ultrasonic observation apparatus comprising:

a processor; and a memory storing computer readable instructions that, when executed by the processor, implement:

a frequency analysis unit that calculates a frequency spectrum for each of a plurality of locations in a predetermined region of the subject by analyzing frequency of the ultrasonic wave at the plurality of locations;

a frequency spectrum approximate equation calculation unit that calculates an approximate equation of the frequency spectrum at the each location calculated by the frequency analysis unit;

a deviation calculation unit that calculates deviation of the frequency spectrum from the approximate equation of the frequency spectrum; and a deviation display image data generation unit that generates information related to the deviation calculated by the deviation calculation unit.

2. The ultrasonic observation apparatus according to claim 1, wherein
the deviation calculation unit further calculates, for the predetermined region, an average of the deviation of the frequency spectrum from the approximate equation of the frequency spectrum, and
the information related to the deviation is the average.

3. The ultrasonic observation apparatus according to claim 1, wherein the deviation display image data generation unit generates deviation display image data by assigning, to the each location, visual information corresponding to the deviation.

4. The ultrasonic observation apparatus according to claim 1, wherein the deviation is a square-sum of deviation defined as a square-sum of difference between intensity of a frequency spectrum corresponding to an arbitrary frequency included in a predetermined band of the frequency spectrum and intensity of an approximate equation of the frequency spectrum.

5. The ultrasonic observation apparatus according to claim 1, wherein the deviation is a deviation area defined as an area surrounded by the frequency spectrum and the approximate equation in the predetermined band of the frequency spectrum when the frequency is expressed along a horizontal axis and intensity of the frequency spectrum is expressed along a vertical axis.

6. The ultrasonic observation apparatus according to claim 1, wherein the frequency spectrum approximate equation calculation unit includes:
an attenuation correction unit that performs, with respect to the frequency spectrum, attenuation correction of reducing contribution of attenuation generated according to received depth and frequency of an ultrasonic wave when the ultrasonic wave is propagated; and
an approximation unit that calculates, by regression analysis, an approximate equation of the frequency spectrum corrected by the attenuation correction unit.

7. The ultrasonic observation apparatus according to claim 6, wherein the approximate equation is a linear equation having frequency as a variable.

8. The ultrasonic observation apparatus according to claim 1, wherein:
the computer readable instructions, when executed by the processor, further implement:
a signal amplification unit that amplifies a signal of an ultrasonic wave received from the subject by an amplification factor according to received depth;
a B-mode image data generation unit that converts an amplitude of the signal of the ultrasonic wave amplified by the signal amplification unit into luminance to generate B-mode data to be displayed; and
an amplification correction unit that performs, with respect to the signal of the ultrasonic wave amplified by the signal amplification unit, amplification correction of making amplification factor constant regardless of received depth; and
wherein the frequency analysis unit analyzes frequency of the signal of the ultrasonic wave subjected to the amplification correction by the amplification correction unit.

9. A method of operating an ultrasonic observation apparatus that transmits an ultrasonic wave to a subject, receives the ultrasonic wave reflected by the subject, and performs image display based on the received ultrasonic wave, the apparatus comprising a processor, the method comprising:
calculating, by use of the processor, a frequency spectrum for each of a plurality of locations in a predetermined region of the subject by analyzing frequency of the ultrasonic wave at the plurality of locations;
calculating, by use of the processor, an approximate equation of the frequency spectrum at the each location, by approximating the frequency spectrum of the each location;
calculating, by use of the processor, deviation of the frequency spectrum from the approximate equation of the frequency spectrum; and
generating, by use of the processor, information related to the deviation.

10. A non-transitory computer readable recording medium storing an executable program that instructs a processor to execute:
calculating a frequency spectrum for each of a plurality of locations in a predetermined region of a subject by analyzing frequency of an ultrasonic wave at the plurality of locations;
calculating an approximate equation of the frequency spectrum at the each location, by approximating the frequency spectrum of the each location;
calculating deviation of the frequency spectrum from the approximate equation of the frequency spectrum; and
generating, information related to the deviation.

* * * * *